United States Patent
Kometas

(10) Patent No.: US 6,511,322 B1
(45) Date of Patent: Jan. 28, 2003

(54) SELF-LIMITING OCCLUSION REDUCTION BURR AND METHOD OF USE

(76) Inventor: Athas N. Kometas, 3162 S. Atlantic Ave., Daytona Beach Shores, FL (US) 32118

( * ) Notice: Subject to any disclaimer, the term of this patent is extended or adjusted under 35 U.S.C. 154(b) by 0 days.

(21) Appl. No.: 09/893,951

(22) Filed: Jun. 29, 2001

(51) Int. Cl.[7] ................................................ A61C 3/06
(52) U.S. Cl. ....................................................... 433/166
(58) Field of Search ................................. 433/165, 166; 408/85, 86, 241 B; 407/54, 34

(56) References Cited

U.S. PATENT DOCUMENTS

| | | |
|---|---|---|
| 2,280,927 A | 4/1942 | Phillips |
| 2,453,696 A | 11/1948 | Brooks |
| 2,901,826 A * | 9/1959 | Kline et al. ................ 433/165 |
| 3,101,546 A * | 8/1963 | Thomas ...................... 433/166 |
| 3,309,772 A * | 3/1967 | Lieb et al. ................. 433/166 |
| 3,576,076 A | 4/1971 | Weissman |
| 4,389,192 A * | 6/1983 | Neuwirth .................... 433/166 |
| 4,526,542 A | 7/1985 | Kochis |
| 4,609,352 A * | 9/1986 | Riitano ....................... 433/165 |
| 4,834,655 A * | 5/1989 | Kyotani ...................... 433/166 |
| 4,854,871 A | 8/1989 | Weissman |
| 5,100,322 A | 3/1992 | Weissman |
| 5,403,187 A | 4/1995 | Wauchope |
| 5,575,650 A * | 11/1996 | Niznick et al. ............. 433/165 |
| 5,839,897 A | 11/1998 | Bordes |
| 5,868,572 A | 2/1999 | Lazzara et al. |
| 5,890,897 A | 4/1999 | Kruger et al. |
| 5,971,758 A | 10/1999 | Hugo et al. |
| 6,235,035 B1 * | 5/2001 | Boukhris .................... 433/165 |
| 6,319,005 B1 * | 11/2001 | Hollander et al. .......... 433/165 |

* cited by examiner

Primary Examiner—Todd E. Manahan
(74) Attorney, Agent, or Firm—Paul S. Rooy

(57) ABSTRACT

A self-limiting occlusal reduction burr and method of use. The self-limiting occlusal reduction burr comprises a shank rigidly attached to one end of a conical shoulder, and a burr rigidly attached to an opposite end of the shoulder. The shank, shoulder, and burr are all axially symmetrical about an axis. A shoulder angle is defined by a shoulder outside surface and the axis, and in the preferred embodiment was 39°±20°. The self-limiting occlusal reduction burr may include indicia specifying a length of said burr and/or a diameter of said burr. The method of use includes the steps of determining an appropriate depth reduction required for a given tooth surface, selecting a self-limiting occlusal reduction burr having a burr length and/or burr diameter sized to yield the depth reduction determined, making a groove pattern using the self-limiting occlusal reduction burr selected, and using said self-limiting occlusal reduction burr to connect said grooves in order to yield a tooth reduction of said depth previously determined.

13 Claims, 4 Drawing Sheets

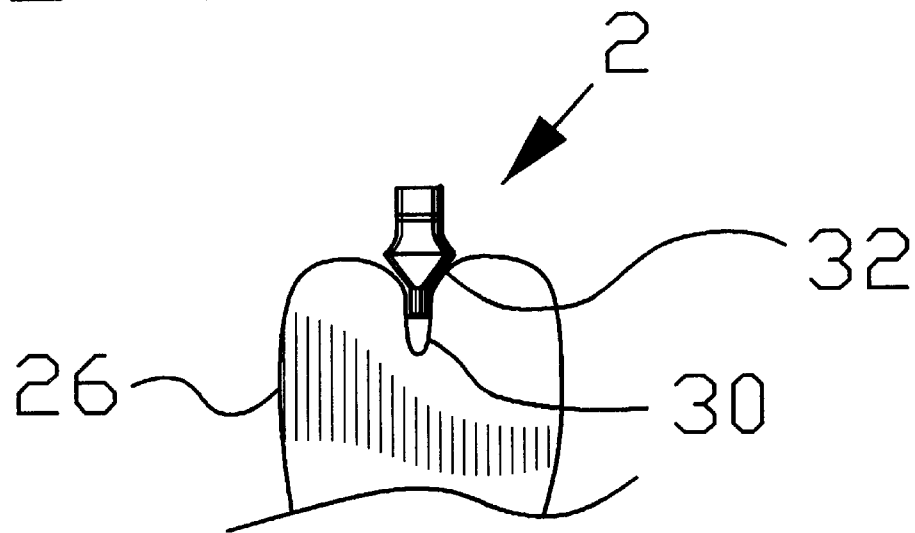
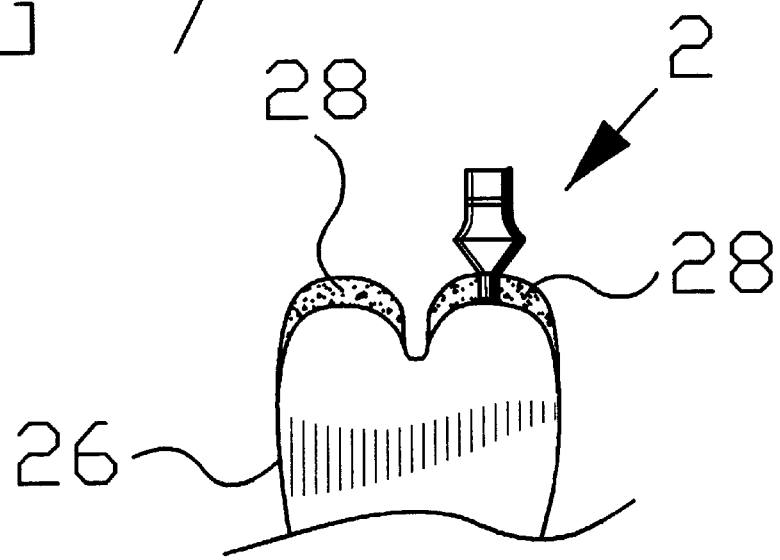

SELF-LIMITING OCCLUSION REDUCTION BURR AND METHOD OF USE

BACKGROUND OF THE INVENTION

1. Field of the Invention

This invention relates to dental burrs, and in particular to a self-limiting occlusal reduction burr and method of use.

2. Background of the Invention

One of the more common dental procedures currently performed is the installation of a crown on a tooth whose state of decay is such that a filling is not a viable option. The tooth must first be prepared by removal of sufficient tooth material so that a ceramist can create a crown whose appearance is realistic. At the same time, excessive tooth material should not be removed during this preparation step, in order that the maximum feasible amount of good tooth be left intact. The problem of removing the correct amount of tooth material becomes more difficult where occlusal grooves are present. In this case, the deepest part of the occlusal groove should be reached by the reduction tool used, so that enough material is removed.

Existing Designs

One approach suggested to permit tooth reductions of a pre-determined depth to be made is illustrated in U.S. Pat. Nos. 2,280,927, 5,403,187, 4,526,542, 3,576,076, 5,100,322, and 5,890,897, granted to Phillips, Wauchope, Kochis, Weissman, Weissman, and Kruger et al. respectively. The apparatuses of these patents all incorporate a disc-shaped drill stop attached to a drill. When the drill has progressed to a certain depth, the drill stop impinges on the tooth being reduced, and prevents further reduction depth from being achieved.

There are a number of problems associated with this approach. During the tooth preparation step, cooling air/water spray must be constantly played on the cutting surface, in order to prevent over-heating of the tooth being reduced. If insufficient cooling is achieved, the tooth could overheat and suffer nerve damage. Because these prior art disc-shaped stops are possessed of flat faces facing the tooth, it is difficult to get the cooling air/water spray into contact with the drill cutting edges.

Another problem is that the flat faces adjacent the tooth prevent the cutting edge from adequately penetrating the tooth in order to remove sufficient tooth material from the bottom of occlusal grooves. If insufficient material is removed from the tooth being prepared, then it is difficult for the ceramist to make the crown appear realistic.

SUMMARY OF THE INVENTION

Accordingly, it is an object of the present invention to provide a self-limiting occlusal reduction burr which can quickly and easily reduce a tooth surface to a pre-determined depth. Design features allowing this object to be accomplished include a burr having a pre-determined burr length, and a shoulder. Advantages associated with the accomplishment of this object include reduced time to make tooth surface reductions, along with the associated cost savings and reduction in patient discomfit time.

It is another object of the present invention to provide a self-limiting occlusal reduction burr whose geometry allows coolant spray to be sent directly to a tooth groove being cut. Design features allowing this object to be accomplished include a conical shoulder having a major diameter and a minor diameter, a shank attached to the shoulder at the shoulder major diameter, and a burr attached to the shoulder at the shoulder minor diameter. Benefits associated with the accomplishment of this object include better tooth cooling during the reduction operation, consequently less chance of tooth nerve damage, and the associated reduction in patient discomfit.

It is still another object of this invention to provide a self-limiting occlusal reduction burr capable of removing sufficient material from fissures. Design features enabling the accomplishment of this object include a conical shoulder having a major diameter and a minor diameter, a shank attached to the shoulder at the shoulder major diameter, and a burr attached to the shoulder at the shoulder minor diameter. Advantages associated with the realization of this object include more accurate tooth material removal and crowns whose appearance is more realistic.

It is another object of the present invention to provide a method of use for a self-limiting occlusal reduction burr which provides for quick and accurate reduction of a tooth in preparation for attachment of a crown. Method steps allowing this object to be accomplished include determining an appropriate depth reduction required for a given tooth surface, selecting a self-limiting occlusal reduction burr having a burr length and/or burr diameter sized to yield the depth reduction previously determined, making a groove pattern using the self-limiting occlusal reduction burr selected, and using the self-limiting occlusal reduction burr to connect the grooves in order to yield a tooth reduction of the depth previously determined. Benefits associated with the accomplishment of this object include reduced time to make tooth surface reductions, along with the associated cost savings and reduction in patient discomfit time.

BRIEF DESCRIPTION OF THE DRAWINGS

The invention, together with the other objects, features, aspects and advantages thereof will be more clearly understood from the following in conjunction with the accompanying drawings.

Four sheets of drawings are provided. Sheet one contains FIG. 1. Sheet two contains FIGS. 2 and 3. Sheet three contains FIGS. 4 and 5. Sheet four contains FIGS. 6 and 7.

FIG. 6 is a side view of a self-limiting occlusal reduction burr in position, ready to start making a groove into a tooth having a fissure.

FIG. 7 is a side view of a self-limiting occlusal reduction burr making a groove into a tooth having a fissure.

DETAILED DESCRIPTION OF THE PREFERRED EMBODIMENT

Figure 1:
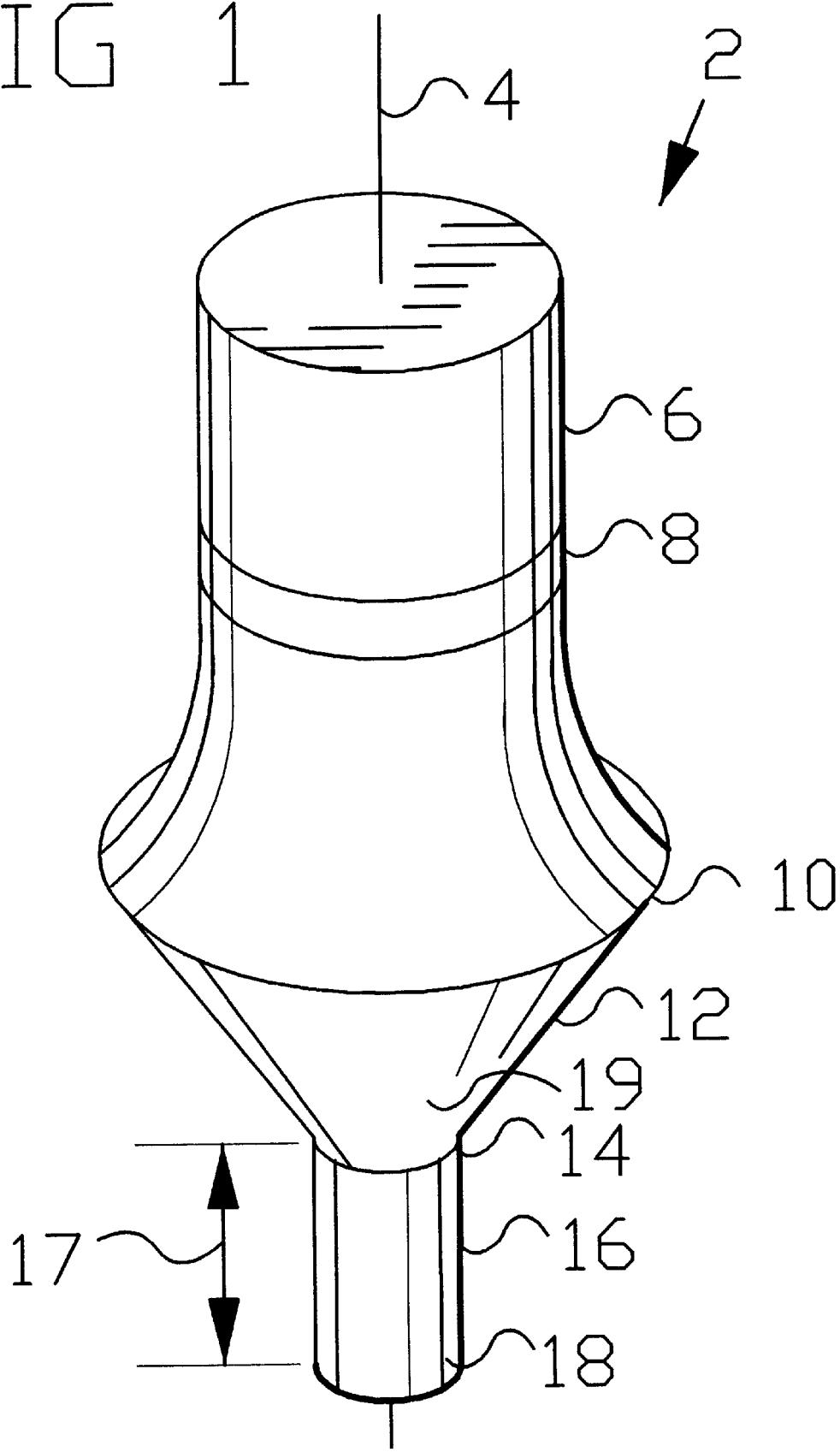
FIG. 1 is a front isometric view of a self-limiting occlusal reduction burr.

FIG. 1 is a front isometric view of self-limiting occlusal reduction burr 2. Self-limiting occlusal reduction burr 2 comprises shank 6 and burr 16 attached to opposite ends of shoulder 12. Shank 6 bears indicia 8 which identifies the size groove which may be cut into a tooth using self-limiting occlusal reduction burr 2. Shoulder 12 is conical in shape, and comprises shoulder major diameter 10 at one end, and shoulder minor diameter 14 at an opposite end. Shank 6 is rigidly attached to shoulder 12 at shoulder major diameter 10, and burr 16 is rigidly attached to shoulder 12 at shoulder minor diameter 14.

Burr 16 comprises burr abrasive surface 18, which is used to cut grooves 28 and tooth reductions 34 into tooth 26. In the preferred embodiment, burr abrasive surface 18 was diamond powder, carbide, tool steel, or other appropriate abrasive surface capable of abrading tooth material.

In use, self-limiting occlusal reduction burr 2 rotates at high speed about axis 4. Thus, shank 6, shoulder 12 and burr 16 are all axially symmetrical about axis 4, that is to say, the cross-sectional shapes of shank 6, shoulder 12 and burr 16 taken at a cut perpendicular to axis 4 would all be circular.

Figure 2:
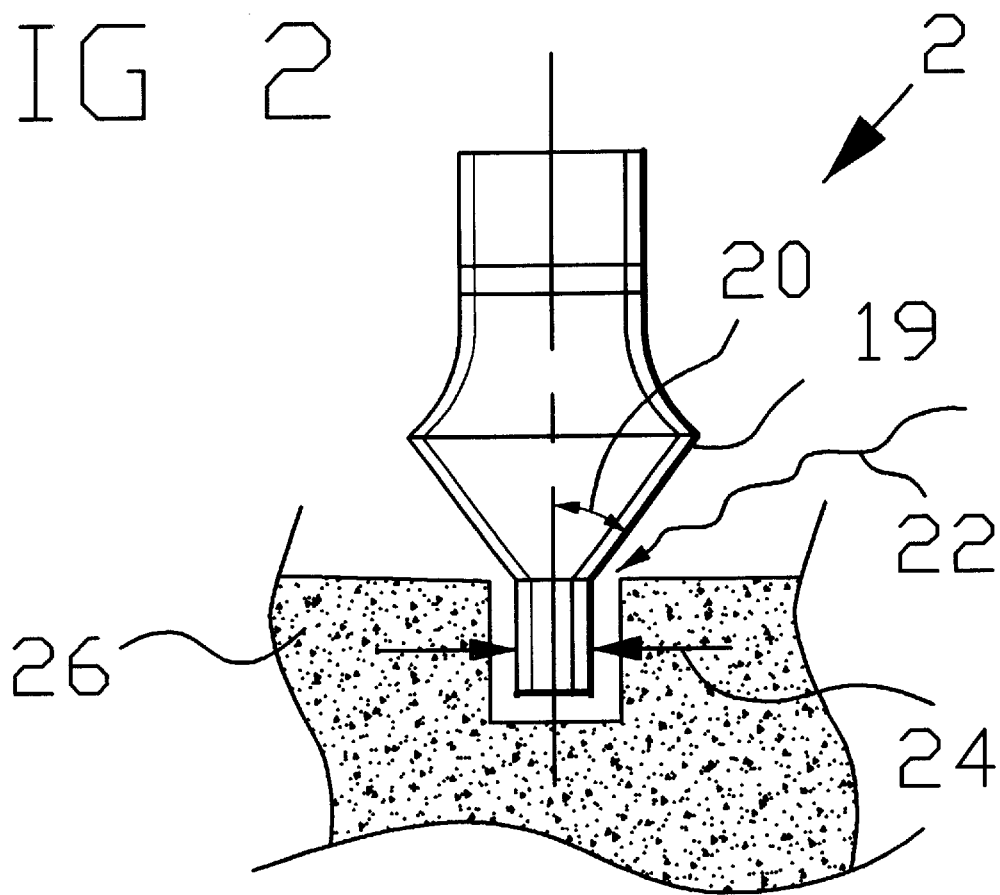
FIG. 2 is a side view of a self-limiting occlusal reduction burr cutting a groove in a tooth.

Defining dimensions of burr 16 include burr length 17 and burr diameter 24. Referring now also to FIG. 2, defining dimensions of shoulder 12 include shoulder major diameter 10, shoulder minor diameter 14, and shoulder angle 20, which is the side view angle between shoulder outer surface 19 and axis 4. In the preferred embodiment, shoulder angle 20 was 39°±20°.

Figure 3:
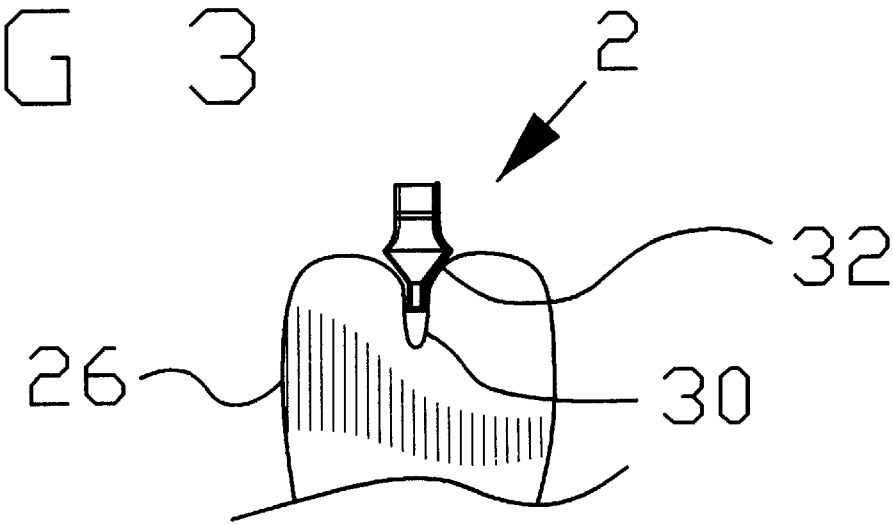
FIG. 3 is a side view of a self-limiting occlusal reduction burr in position, ready to start making a groove into a tooth having a fissure.

There are two main reasons for shoulder angle 20 being 39°±20°. First, shoulder angle 20 permits coolant spray 22 to be sprayed directly to where it is needed most: the interface between self-limiting occlusal reduction burr 2 and tooth 26 at groove 28. Second, shoulder angle 20 allows self-limiting occlusal reduction burr 2 to be positioned properly over fissure 30 (as is illustrated in FIG. 3) in order to permit a groove 28 to be cut to the proper depth in and around fissure 30 as depicted in FIGS. 6 and 7. FIG. 6 is a side view of a self-limiting occlusal reduction burr 2 in position, ready to start making a groove 28 into a tooth 26 having a fissure 30. FIG. 7 is a side view of a self-limiting occlusal reduction burr 2 making a groove 28 into a tooth 26 having a fissure 30.

Note that in the case of making a reduction in tooth 26 having fissure 30, the correct place to measure the depth of groove 28 is from fissure shoulder 32. This is possible to do using the instant self-limiting occlusal reduction burr because of shoulder angle 20.

The depth groove 28 which may be cut using self-limiting occlusal reduction burr 2 is determined by burr length 17 and burr diameter 24. Either or both these dimensions are identified by means of indicia 8 inscribed on shank 6. Indicia 8 may be any means of communicating this information, including but not limited to numbers, letters, color bands, etc.

Figure 4:
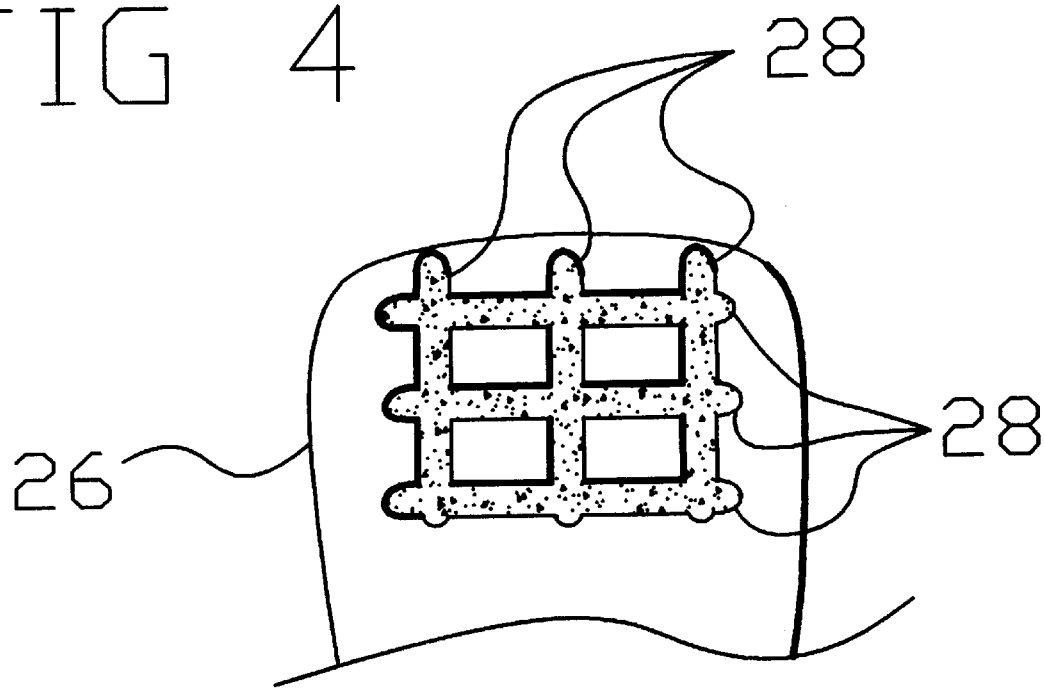
FIG. 4 is a side view of tooth into which a groove pattern has been cut.
Figure 5:
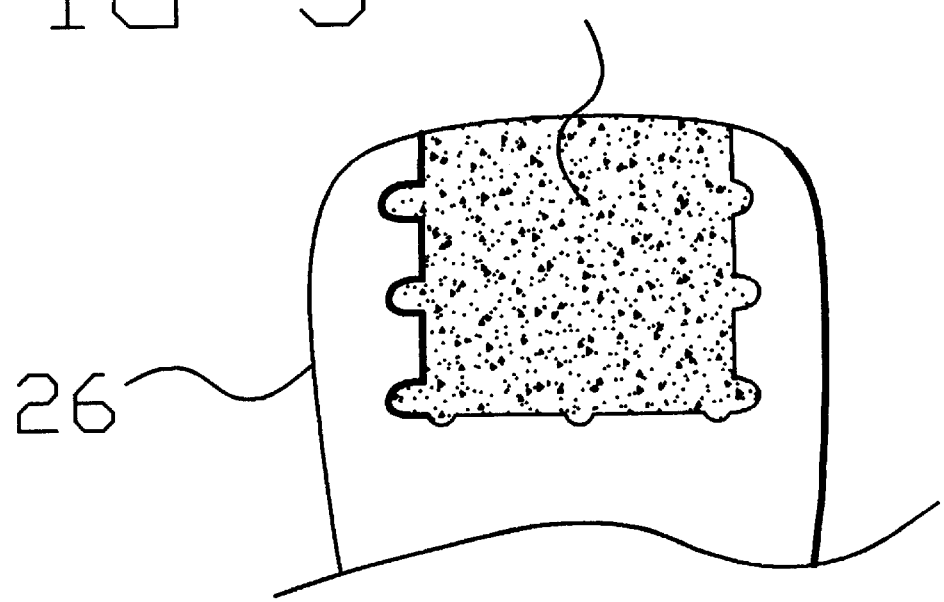
FIG. 5 is a side view of tooth into which a reduction has been made.

FIG. 4 is a side view of tooth 26 into which a groove 28 pattern has been cut. FIG. 5 is a side view of tooth 26 into which tooth reduction 34 has been made. FIGS. 4 and 5 illustrate two of the instant method steps of tooth reduction in preparation for attaching a crown.

First, a self-limiting occlusal reduction burr 2 of correct burr 16 dimensions is selected. This step is important, because burr length 17 serves as a visual aid to make grooves 28 of the correct depth. For example, a porcelain to gold crown typically requires a tooth reduction of 2.5 mm, a porcelain crown requires 2.0 mm, and a pure gold crown 1.5 mm. The side of the tooth facing the outside of the mouth may require a 2.5 mm reduction, while the back side of the tooth may be reduced only 1.5 mm.

In use, self-limiting occlusal reduction burr 2 is used to make a groove of depth such that shoulder minor diameter 14 is flush with the surface of the tooth 26 being prepared.

As soon as self-limiting occlusal reduction burr 2 has penetrated the tooth until shoulder minor diameter 14 is flush with the tooth surface, self-limiting occlusal reduction burr 2 is moved sideways in order to produce a constant-depth groove.

A pattern of these constant-depth grooves 28 is cut into tooth 26 as may be observed in FIG. 4. Once the groove 28 pattern has been made, self-limiting occlusal reduction burr 2 is used to connect the grooves 28 into tooth reduction 34 as is shown in FIG. 5. Tooth reduction 34 is made of appropriate size and depth as required for the crown to be attached.

Thus, the instant method of use for a self-limiting occlusal reduction burr 2 comprises the following steps:

A. Determining an appropriate depth reduction required for a given tooth surface;

B. Selecting a self-limiting occlusal reduction burr having a burr length and/or burr diameter sized to yield the depth reduction determined in step A;

C. Making a groove pattern using the self-limiting occlusal reduction burr selected in step B, making each groove only deep enough for a self-limiting occlusal reduction burr shoulder minor diameter to be flush with the tooth surface when the burr is touching the bottom of the groove; and D. Using the self-limiting occlusal reduction burr to connect the grooves in order to yield a tooth reduction of the depth determined in step A.

While a preferred embodiment of the invention has been illustrated herein, it is to be understood that changes and variations may be made by those skilled in the art without departing from the spirit of the appending claims.

DRAWING ITEM INDEX 2 self-limiting occlusal reduction burr
4 axis
6 shank
8 indicia
10 shoulder major diameter
12 shoulder
14 shoulder minor diameter
16 burr
17 burr length
18 burr abrasive surface
19 shoulder outside surface
20 shoulder angle
22 coolant spray
24 burr diameter
26 tooth
28 groove
30 fissure
32 fissure shoulder
34 tooth reduction

I claim:

1. A self-limiting occlusal reduction burr comprising a shank, a shoulder and an abrasive burr, said shoulder being non-abrasive and conical in shape and comprising a shoulder major diameter at one end and a shoulder minor diameter at an opposite end, said shank being rigidly attached to said shoulder at said shoulder major diameter, and said buff being attached to said shoulder at said shoulder minor diameter.

2. The self-limiting occlusal reduction burr of claim 1 wherein said shank, said shoulder, and said burr are all axially symmetrical about an axis.

3. The self-limiting occlusal reduction burr of claim 2 wherein said shoulder comprises a shoulder outer surface and a shoulder angle, said shoulder angle being defined as an angle between said shoulder outer surface and said axis, said shoulder angle being 39°±20°.

4. The self-limiting occlusal reduction burr of claim 3 wherein said shank further comprises indicia, said indicia specifying a length of said burr and/or a diameter of said burr.

5. The self-limiting occlusal reduction burr of claim 4 wherein said burr is coated with abrasive.

6. The self-limiting occlusal reduction burr of claim 5 wherein said burr abrasive is diamond powder.

7. The self-limiting occlusal reduction burr of claim 6 wherein said burr is a cylinder whose axis corresponds to said self-limiting occlusal reduction burr axis.

8. A self-limiting occlusal reduction burr comprising a shank, a shoulder and an abrasive burr all axially symmetrical about an axis, said shoulder being non-abrasive and conical in shape and comprising a shoulder outside surface, a shoulder angle, a shoulder major diameter at one end and a shoulder minor diameter at an opposite end, said shank being rigidly attached to said shoulder at said shoulder major diameter, and said burr being attached to said shoulder at said shoulder minor diameter, said shoulder angle being defined as an angle between said shoulder outer surface and said axis, and said shoulder angle measures 39°±20°.

9. The self-limiting occlusal reduction burr of claim 8 wherein said burr is covered with abrasive.

10. The self-limiting occlusal reduction burr of claim 9 further comprising indicia specifying a length of said burr and/or a diameter of said burr.

11. A method of use of self-limiting occlusal reduction burr, said self-limiting occlusal reduction burr comprising a shank, a shoulder and an abrasive burr all axially symmetrical about an axis, said shoulder being non-abrasive and conical in shape and comprising a shoulder outside surface, a shoulder angle, a shoulder major diameter at one end and a shoulder minor diameter at an opposite end, said shank being rigidly attached to said shoulder at said shoulder major diameter, and said burr being attached to said shoulder at said shoulder minor diameter, said method comprising the steps of:

A. Determining an appropriate depth reduction required for a given tooth surface;

B. Selecting a self-limiting occlusal reduction burr having a burr length and/or burr diameter sized to yield the depth reduction determined in step A;

C. Making a groove pattern using the self-limiting occlusal reduction buff selected in step B substantially perpendicular to said tooth surface, whereby the conical shoulder shape provides enhanced cooling and improved access to said tooth surface, making each groove only deep enough for said self-limiting occlusal reduction burr shoulder minor diameter to be flush with said tooth surface when the burr is touching a bottom of said grooves; and D. Using said self-limiting occlusal reduction burr to connect said grooves in order to yield a tooth reduction of said depth determined in step A.

12. The method of use of a self-limiting occlusal reduction burr of claim 11 comprising the further step of spraying coolant spray onto said burr in order to prevent said tooth from over-heating.

13. The method of use of a self-limiting occlusal reduction burr of claim 11 comprising the further step of measuring a groove made with said self-limiting occlusal reduction burr into a tooth fissure such that a correct groove depth is achieved when said shoulder minor diameter is flush with a fissure shoulder.

* * * * *

UNITED STATES PATENT AND TRADEMARK OFFICE
CERTIFICATE OF CORRECTION

PATENT NO.     : 6,511,322 B1                                           Page 1 of 1
DATED          : January 28, 2003
INVENTOR(S)    : Kometas, Athas N.

It is certified that error appears in the above-identified patent and that said Letters Patent is hereby corrected as shown below:

Column 4,
Line 61, "buff..." should be -- burr... --

Column 5,
Line 31, "A method of use of self-limiting..." should be -- A method of use of a self-limiting... --

Column 6,
Line 13, "buff..." should be -- burr... --

Signed and Sealed this

Third Day of June, 2003

JAMES E. ROGAN
*Director of the United States Patent and Trademark Office*